United States Patent [19]

Weber et al.

[11] Patent Number: 5,141,926

[45] Date of Patent: Aug. 25, 1992

[54] ERYTHROMYCIN DERIVATIVES

[75] Inventors: J. Mark Weber, Evanston; James B. McAlpine, Libertyville, both of Ill.

[73] Assignee: Abbott Laboratories, Abbott Park, Ill.

[21] Appl. No.: 510,483

[22] Filed: Apr. 18, 1990

[51] Int. Cl.$^5$ ...................... A61K 31/71; C07H 17/08
[52] U.S. Cl. ........................ 514/29; 536/7.2; 435/76; 435/882
[58] Field of Search ............... 536/7.1; 514/29; 435/882, 76

[56] References Cited

U.S. PATENT DOCUMENTS 4,331,803  5/1982  Watanabe et al. ............... 536/7.2
4,874,748 10/1989  Katz et al. ....................... 536/7.2

Primary Examiner—Johnnie R. Brown
Assistant Examiner—Elli Peselev
Attorney, Agent, or Firm—Andreas M. Danckers

[57] ABSTRACT

Novel 6-deoxyerythromycin derivatives are disclosed, as are methods for their preparation and use as antiinfective agents. The compounds of the invention include 6-deoxyerythromycins and 6-deoxy-15-norerythromycins which are represented by the structural formula

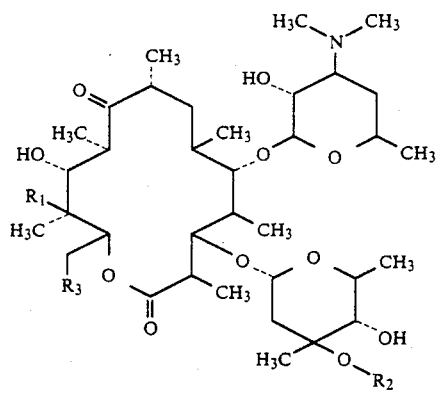

in which $R_1$ is selected from OH and H, and $R_2$ and $R_3$ are independently selected from H and $CH_3$, as well as the pharmaceutically acceptable salts and esters of the above compounds. Additionally disclosed are genetically modified microorganisms which produce the compounds of the invention and means for the preparation of those microorganisms.

6 Claims, 10 Drawing Sheets

Construction of Plasmid pMW56-H23

FIGURE 3

DNA Sequence of the eryF Gene Responsible for C-6 Hydroxylation in S. erythraea

```
GGATC CCGAT CGTGT CGGAG GAAGA GGCCA AGTCG CGCCG CCCCG ACCAG
CTGCT GGTGC TGCCC TGGAT CTACC GCGAC GGGTT CGTCG AACGC GAGCA
GGAGT TCCTC GCTGG CGGCG GAAAG CTGAT CTTCC CCCTA CCCCG ACTGG
AAGTC GTATG ACGAC CGTTC CCGAT CTCGA AAGCG ACTCC TTCCA CGTCG
ACTGG TACCG CACCT ACGCC GAGCT GCGCG AGACC GCGCC GGTGA CGCCG   250

GTGCG CTTCC TCGGC CAGGA CGCGT GGCTG GTCAC CGGCT ACGAC GAGGC
GAAGG CCGCG CTGAG CGACC TGCGC CTGAG CAGCG ACCCG AAGAA GAAGT
ACCCG GGCGT GGAGG TCGAG TTCCC GGCAT ACCTC GGTTT CCCCG AGGAC
GTGCG GAACT ACTTC GCCAC CAACA TGGGC ACCAG CGACC CGCCG ACCCA
CACCC GGCTG CGCAA GCTGG TGTCG CAGGA GTTCA CCGTC CGCCG CGTGG   500

AGGCG ATGCG GCCCC GCGTC GAGCA GATCA CCGCG GAGCT GCTCG ACGAG
GTGGG CGACT CCGGC GTGGT CGACA TCGTC GACCG CTTCG CCCAC CCGCT
GCCCA TCAAG GTCAT CTGCG AGCTG CTCGG CGTCG ACGAG AAGTA CCGCG
GGGAG TTCGG GCGGT GGAGC TCGGA GATCC TGGTC ATGGA CCCGG AGCGG
GCCGA ACAGC GCGGG CAGGC GGCCA GGGAG GTCGT CAACT TCATC CTCGA   750

CCTGG TCGAG CGCCG CCGCA CCGAG CCCGG CGACG ACCTG CTGTC CGCGC
TGATC AGGGT CCAGG ACGAC GATGA CGGTC GGCTC AGCGC CGACG AGCTG
ACCTC CATCG CGCTG GTGCT GCTGC TGGCC GGTTT CGAGG CGTCG GTGAG
CCTCA TCGGG ATCGG CACCT ACCTG CTGCT CACCC ACCCG GACCA GCTCG
CGCTG GTGCG GCGGG ACCCG TCGGC GCTGC CCAAC GCCGT CGAGG AGATC   1000
```

FIGURE 3 (Continued)

```
CTGCG CTACA TCGCT CCGCC GGAGA CCACC ACGCG CTTCG CCGCG GAGGA
GGTGG AGATC GGCGG TGTCG CGATC CCCCA GTACA GCACG GTGCT GGTCG
CGAAC GGCGC GGCCA ACCGC GACCC GAAGC AGTTC CCGGA CCCCC ACCGC
TTCGA CGTCA CCCGC GACAC CCGCG GCCAC CTGTC GTTCG GCAG GGCAT
CCACT TCTGC ATGGG CCGGC CGCTG GCCAA GCTGG AGGGC GAGGT GGCGC   1250

TGCGG GCGCT GTTCG GCCGC TTCCC CGCTC TGTCG CTGGG AATCG ACGCC
GACGA CGTGG TGTGG CGGCG TTCGC TGCTG CTGCG GGGCA TCGAC CACCT
ACCGG TGCGG CTCGA CGGAT GAGCA CCTGG CTGCG GCGGT TCGGT CCTCC
```

Start Codon = ATG (bp 158-169)
Stop Codon = TGA (bp 1370-1372)
Bold Print = eryF Gene

FIGURE 4

503 bp Recognition Sequence of Integrative Plasmid pMW56-H23

```
          10         20         30         40         50
GATCT CGAAA GCGAC TCCTT CCAGG TCGAC TGGTA CCGCA CCTAC GCCGA
GCTGC GCGAG ACCGC GCCGG TGACG CCGGT GCGCT TCCTC GGCCA GGACG
CGTGG CTGGT CACCG GCTAC GACGA GGCGA AGGCC GCGCT GAGCG ACCTG
CGCCT GAGCG ACCCG AAGAA GAAGT ACCCG GGCGT GGAGG TCGAG TTCCC
GGCAT ACCTC GGTTT CCCCG AGGAC GTGCG GAACT ACTTC GCCAC CAACA  250

TGGGC ACCAG CGACC CGCCG ACCCA CACCC GGCTG CGCAA GCTGG TGTCG
CAGGA GTTCA CCGTC CGCCG CGTGG AGGCG ATGCG GCCCC GCGTC GAGCA
GATCA CCGCG GAGCT GCTCG ACGAG GTGGG CGACT CCGGC GTGGT CGACA
TCGTC GACCG CTTCG CCCAC CCGCT GCCCA TCAAG GTCAT CTGCC AGCTG
CTCGC GTCGA CGAGA AGTAC CGCGG GGAGT CGGGC GGTG GAGCT CGGAG  500

ATC
```

Restriction Map of Plasmid pMW56-H23

Integrative Transformation of S. erythraea by Plasmid pMW56-H23

Chromosomal Map of S. erythraea
Erythromycin Biosynthetic Gene Cluster

500 MHz Proton NMR Spectrum of 6-Deoxy-15-norerythromycin A

500 MHz Proton NMR Spectrum of 6-Deoxy-15-norerythromycin C

ERYTHROMYCIN DERIVATIVES

TECHNICAL FIELD

The present invention relates to a novel class of erythromycin derivatives. In particular, the present invention relates to 6-deoxyerythromycin compounds, the use of these compounds as antibiotics and a method for preparing them.

BACKGROUND OF THE INVENTION

Erythromycins, and in particular erythromycin A, are clinically useful, broad-spectrum macrolide antibiotics produced by the gram-positive bacterium *Saccharopclyspora erythraea* (formerly *Streptomyces erythreus*). However, a major drawback of erythromycins is their poor acid stability, which can result in diminished and erratic oral absorption.

Numerous erythromycin derivatives have been chemically synthesized in an attempt to produce compounds with improved acid stability without loss of antibacterial activity. (9S)9-Dihydroerythromycin A (which carries a 9-hydroxy group in place of the 9-keto group) has been described (Wiley et al., *J. Amer. Chem. Soc.*, 77:3676-3677 (1955)). Erythromycylamine and erythromycin oxime in which the 9-keto group is replaced, respectively, by an amino or oxime group have also been described (GB 1 100 504; Massey et al, *Tetrahedron Letters*, 2:157-160 (1970)), as have various erythromycin oxime ethers (U.S. Pat. No. 3,681,326, U.S. Pat. No. 3,869,445 and U.S. Pat. No. 4,063,014). 6-O-methylerythromycin (clarithromycin) and 6,11-di-O-methyl-erythromycin A are described U.S. Pat. No. 4,743,593.

Although the above derivatives exhibit improved acid stability, the synthetic methods by which they are produced are expensive and can produce low yields. Moreover, the acid instability of the starting material (i.e., erythromycin) has hampered efforts to synthesize more active derivatives.

There is therefore a need for improved acid-stable erythromycin derivatives and, moreover, for derivatives which are microbially produced and which thereby circumvent the inefficiency of the aforementioned synthetic methods or at least provide a more favorable starting material for the preparation of synthetic derivatives.

SUMMARY OF THE INVENTION

The compounds and mixtures of the present invention include 6-deoxyerythromycins and 6-deoxy-15-norerythromycins which are represented by structural Formula I:

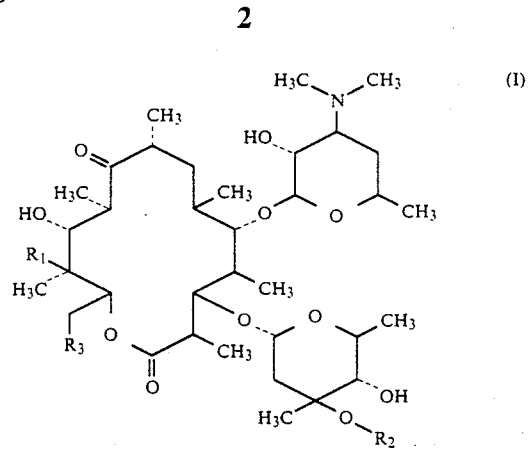

in which $R_1$ is selected from OH and H, and $R_2$ and $R_3$ are independently selected from H and $CH_3$ Also included among the compounds of the invention is the biosynthetic intermediate 3-α-mycarosyl-6-deoxyerythronolide B, as well as the pharmaceutically acceptable salts and esters of the compounds of Formula I.

The method of the present invention includes the genetic modification of an erythromycin-producing microorganism, so that the microorganism is transformed into a strain producing the compounds of the invention. The microorganismal genome is genetically modified in a region which is essential for the C-6 hydroxylation of an intermediate in the erythromycin biosynthetic pathway. In a particular embodiment of the invention, the microorganismal DNA to be modified is in the genomic region responsible for the hydroxylation of 6-deoxyerythronolide B to erythronolide B by the *S. erythraea* cytochrome P450 monooxygenase system.

According to one aspect of the method of the invention, transformation of an erythromycin-producing microorganism into a 6-deoxyerythromycin-producing strain is accomplished by integrating, via homologous recombination, a mutagenic plasmid into a portion of the microorganismal DNA which is responsible for C-6 hydroxylation. This integrative plasmid is constructed to be capable of being stably maintained in the microorganism, i.e., of being passed from a transformed cell to its similarly transformed progeny. In a particular embodiment of the invention, the integrative plasmid is constructed using a DNA fragment which is homologous to a portion of the DNA essential for the operation of the cytochrome P450 monooxygenase system in *S. erythraea*.

According to a further aspect of the method of the invention, a 6-deoxyerythromycin-producing *S. erythraea* transformant is genetically crossed with a second strain of *S. erythaea* which has been selectively bred to produce high levels of erythromycin A. From among the progeny of this cross are selected recombinant microorganisms which retain the ability to produce 6-deoxyerythromycin, but achieve higher yields than those possible with the original transformant strain.

A microorganism embodying the present invention is a novel strain of *S. erythraea* which produces, upon cultivation in an aqueous medium containing assimilable sources of nitrogen and carbon, a compound selected from among 6-deoxyerythromycins A, B, C and D and 6-deoxy-15-norerythromycins A, B, C and D. More preferably, the microorganism of the invention is one which has been crossed with a high-yielding erythromycin producer and which demonstrates an enhanced ability to produce the compounds of the invention.

BRIEF DESCRIPTION OF THE DRAWINGS

The present invention will be more readily appreciated in connection with the accompanying drawings, in which:

FIG. 3 is the DNA sequence of the eryF gene responsible for C-6 hydroxylation in S. erythraea;

FIG. 4 is the DNA sequence of a 503 bp fragment used as recognition sequence in an integrative plasmid of the invention;

DETAILED DESCRIPTION OF THE INVENTION

Figure 1:
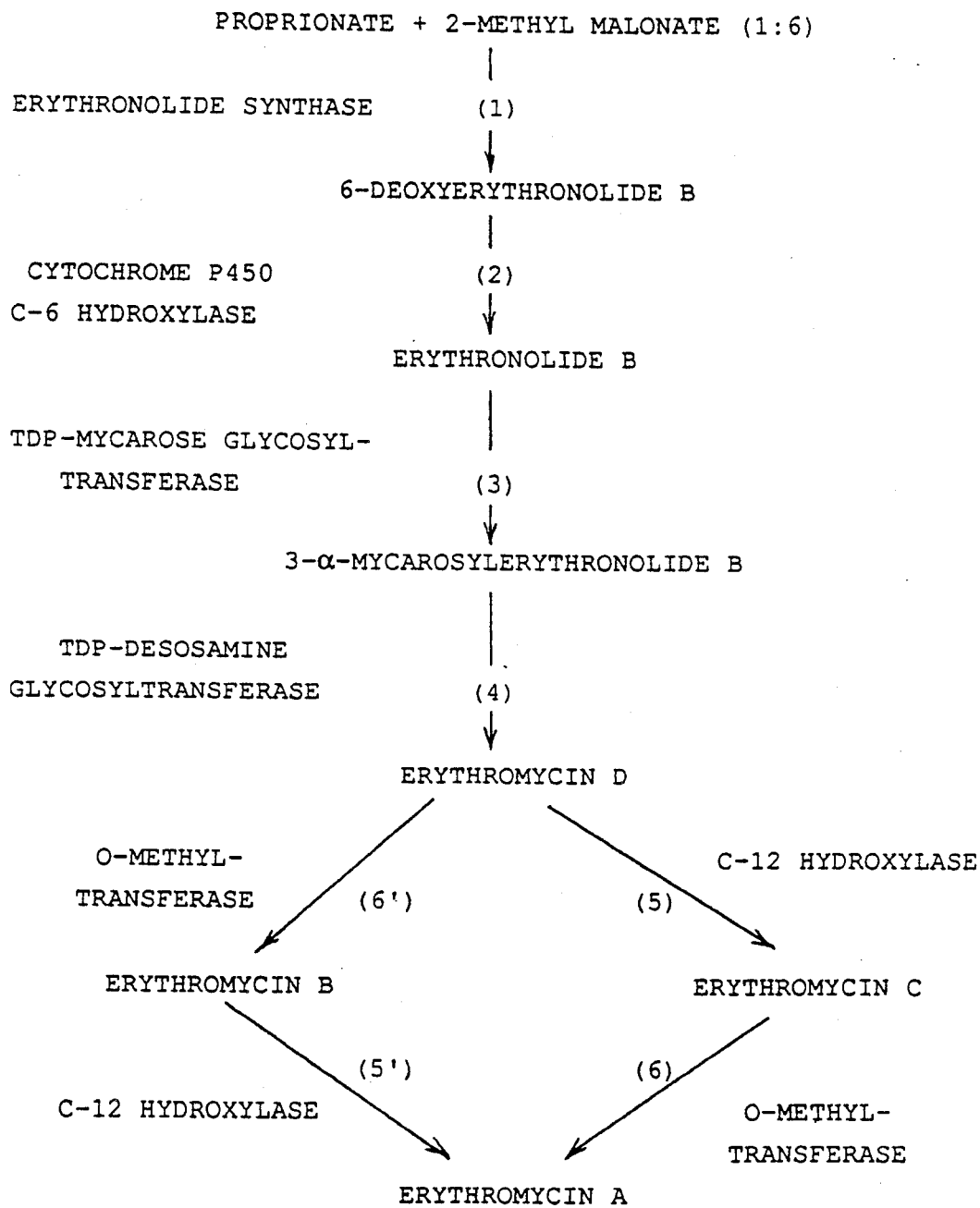
FIG. 1 is a proposed metabolic pathway for the biosynthesis of erythromycin A in S. erythraea.

The present invention provides novel erythromycin derivatives and pharmaceutically acceptable salts and esters thereof, as well as the use of these compounds as antibiotics and a method for their preparation. The compounds of the invention are of structural formula I:

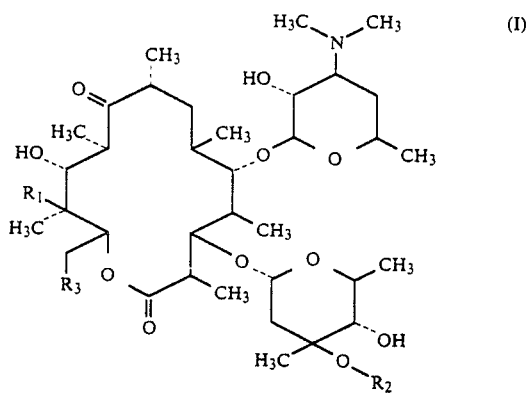

in which $R_1$ is selected from OH and H and $R_2$ and $R_3$ are independently selected from H and $CH_3$. The compounds of Formula I are also referred to herein as 6-deoxyerythromycins A through D and 6-deoxy-15-norerythromycins A through D as follows:

|  | $R_1$ | $R_2$ | $R_3$ |
|---|---|---|---|
| 6-Deoxyerythromycin A | OH | $CH_3$ | $CH_3$ |
| 6-Deoxyerythromycin B | H | $CH_3$ | $CH_3$ |
| 6-Deoxyerythromycin C | OH | H | $CH_3$ |
| 6-Deoxyerythromycin D | H | H | $CH_3$ |
| 6-Deoxy-15-norerythromycin A | OH | $CH_3$ | H |
| 6-Deoxy-15-norerythromycin B | H | $CH_3$ | H |
| 6-Deoxy-15-norerythromycin C | OH | H | H |
| 6-Deoxy-15-norerythromycin D | H | H | H |

These compounds are obtained by growing a genetically modified erythromycin-producing microorganism in culture and then extracting them from the culture medium. In one embodiment of the invention described herein, the microorganism used is the bacterium *Saccharopolyspora erythraea*.

The present invention also provides a method for producing the above compounds, comprising the transformation of a natural or wild-type erythromycin-producing microorganism into a variant producing the desired compounds. In one embodiment of the invention, the resulting transformant is deficient in the cytochrome P450 monooxygenase system which in the wild-type Saccharopolyspora microorganism is responsible for the hydroxylation of 6-deoxyerythronolide B at the C-6 position during erythromycin biosynthesis. Because the remaining steps in the erythromycin biosynthetic pathway continue to function, the compounds of the present invention are produced instead of erythromycins A through D.

The invention also provides, as an example, a particular method for interrupting C-6 hydroxylation, comprising the integration via homologous recombination of a plasmid into the genome of the microorganism. The integrative plasmid is constructed comprising a nucleotide sequence which is homologous to a portion of the microorganismal genome. In one embodiment of the invention, the homology is with a subset of the gene which, in the wild-type microorganism, is responsible for hydroxylation at the C-6 position. Integration of the plasmid at the site of homology separates the gene into two incomplete sequences, neither of which are sufficient for C-6 hydroxylation. Hydroxylation is therefore interrupted so long as the integrative plasmid is stably maintained within the microorganismal genome.

Because a wild-type microorganism is not likely to produce high yields of erythromycin, transformants of such an organism are similarly unlikely to produce commercially useful amounts of 6-deoxyerythromycin. The present invention therefore further provides for the use of high-producing strains to enhance the yields obtained by fermentation of 6-deoxyerythromycin-producing strains. Such high-producing variants, which are commercially available or can be obtained by selectively breeding wild-type microorganisms, can, for example, be cross-bred with 6-deoxyerythromycin-producing transformants or, alternatively, themselves be transformed into high-level 6-deoxyerythromycin producers.

In a preferred embodiment of the method of the invention, a transformant of a wild-type Saccharopolyspora microorganism is genetically crossed with a high producer of erythromycin. The recombinant progeny of this cross are selected for their retention of the ability to produce 6-deoxyerythromycin as well as their capacity for producing high levels of the desired compounds.

Both wild-type transformant and recombinant progeny are representative of the microorganisms of the present invention, which include any producers of erythromycin which have been genetically modified to produce 6-deoxyerythromycin. A preferred embodiment of the microorganisms of the invention, prepared according to the Examples below, is *Saccharopolyspora erythraea* 41R. This crossed strain, which produces significantly higher quantities of 6-deoxyerythromycin than its transformant parent, has been deposited under the terms of the Budapest Treaty with the Agricultural Research Culture Collection, Northern Regional Research Center, U.S. Department of Agriculture, 1815 North University Street, Peoria, IL 61604, United States, and has been accorded accession number NRRL 18643.

The methods of the present invention are widely applicable to all erythromycin-producing microorganisms, of which a non-exhaustive list includes Saccharopolyspora species, *Streptomyces griseoplanus*, Nocardia sp., Micromonospora sp., Arthrobacter sp. and *Streptomyces antibioticus*. Of these, *Saccharopolyspora erythraea* is the most preferred. In the biosynthesis of erythromycin by *S. erythraea*, the compound is believed to be made according to the pathway shown in FIG. 1, in which steps (1) and (2) are the assembly of the 14-membered macrolactone 6-deoxyerythronolide B from propionyl and 2-methylmalonyl thioesters followed by its hydroxylation to erythronolide B; steps (3) and (4) are the formation of the deoxysugars mycarose and desosamine from glucose and their addition to erythronolide B to make erythromycin D; and steps (5) and (6) [or (6') and (5')] are C-12 hydroxylation and C-3" O -methylation to produce erythromycin A.

The earliest intermediate identified in *S. erythraea* erythromycin biosynthesis is 6-deoxyerythronolide B, which is hydroxylated as the next step in the biosynthetic pathway. This hydroxylation is catalyzed by a cytochrome P-450 monooxygenase system requiring two flavoproteins and an iron-sulfur protein (erythrodoxin) which act in conjunction with the 6-hydroxylase (Shafiee, et. al., J. Bacteriol. 170:1548-1553 (1988)).

Interruption of the C-6 hydroxylation step during erythromycin biosynthesis results in the formation of 6-deoxyerythromycin A, as well as other 6-deoxy intermediates of the biosynthetic pathway. One means of interrupting hydroxylation is through the disruption of a cellular gene required for the operation of the cytochrome P-450 monooxygenase system. This can be accomplished by inserting into such a gene an integrative plasmid which is stably maintained in the microorganism, thereby transforming the microorganism into a 6-deoxyerythromycin-producing mutant. Any plasmid which can be integrated into the microorganismal genome and result in the interruption of hydroxylation of 6-deoxyerythronolide can be utilized. The method of the present invention is, however, in no way limited to the use of gene disruption to produce mutants deficient in the hydroxylation of 6-deoxyerythronolide. Other procedures which disrupt the hydoxylase system, such as gene replacement (which involves the removal of specific gene sequences) or chemical or light-induced mutagenesis, can be used to produce the desired genetically modified microorganism.

Although several methods are known in the art for inserting foreign DNA into a plasmid to form an integrative plasmid, the method preferred in accordance with this invention is shown schematically in FIG. 2 and demonstrated in the Examples below. In a preferred embodiment of the present invention, a selectable DNA plasmid is constructed which comprises (a) a fragment of plasmid pIJ702 containing a determinant for replication and a fragment of DNA conferring resistance to the antibiotic thiostrepton (tsr), each of which are functional in Streptomyces; (b) a functional origin of replication and a DNA fragment conferring resistance to the antibiotic ampicillin (amp), each of which are functional in *E. coli*; and (c) a DNA fragment from the ermE region of *S. erythraea*, containing a portion of a gene responsible for the operation of the cytochrome P450 - monooxygenase system and capable as acting as a recognition sequence for plasmid integration. A culture of *E. coli* which contains a plasmid embodying the invention, designated pMW56-H23, has been deposited as above with the Agricultural Research Culture Collection and has been accorded accession number NRRL B18628.

The particular antibiotic resistance genes and functional origins of replication identified above are necessary only inasmuch as they allow for the selection and replication of the desired recombinant plasmids. Other markers and origins of replication may be used in the practice of the invention wherever feasible. Likewise, any recognition sequence may be used which enables the recombinant plasmid to be integrated into a portion of the microorganismal genome necessary for C-6 hydroxylation, and which results in the interruption of hydroxylation. In the preferred organism *S. erythraea*, the recognition sequence may be a fragment comprising a subset of the nucleotide sequence shown in FIG. 3, which is believed to represent the eryF gene coding for C-6 hydroxylase and the adjacent flanking sequences.

An operative recognition sequence, used in the Examples below, is shown in FIG. 4. This 503 bp Sau3A-Sau3A fragment is obtained from a 10 kb HindIII-EcoRI fragment of the cosmid pJI according to the method of the Examples.

Other sequences may be identified which are located elsewhere in the *S. erythraea* genome; these, too, are regarded as within the scope of the present invention. Moreover, in those cases where a portion of the microorganismal genome responsible for C-6 hydroxylation has been sequenced, the plasmid of the invention may be constructed without the use of a partial genomic digest as in the above example. Instead, a recognition sequence may be synthesized de novo and ligated with the necessary origin and resistance fragments to form an integrative plasmid.

The integrative plasmids of the present invention may be used in conjunction with *S. erythraea* and other host strains. The plasmids are useful because they are small, versatile, and may be introduced into a variety of host strains including *S. erythraea* and *E. coli*.

Figure 5:
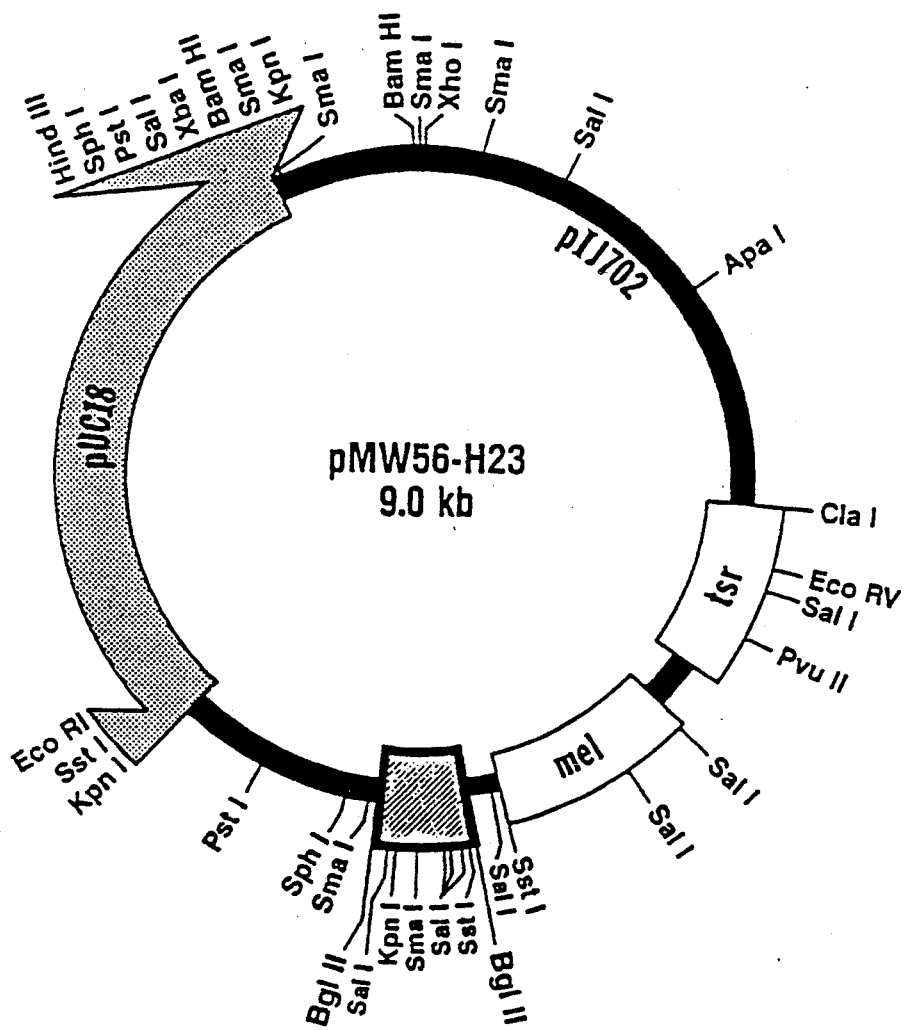
FIG. 5 is a restriction map of plasmid pMW56-H23.

One embodiment of the integrative plasmids of this invention is shown in the restriction map of FIG. 5. Designated herein as pMW56-H23, the plasmid contains the Sau3A-Sau3A fragment of FIG. 4, inserted into a novel plasmid formed by the combination of plasmids pUC18 and pIJ702. The Sau3A sequence is inserted at a unique BglII site, shown in FIG. 5 at the bottom of the plasmid.

Figure 6:
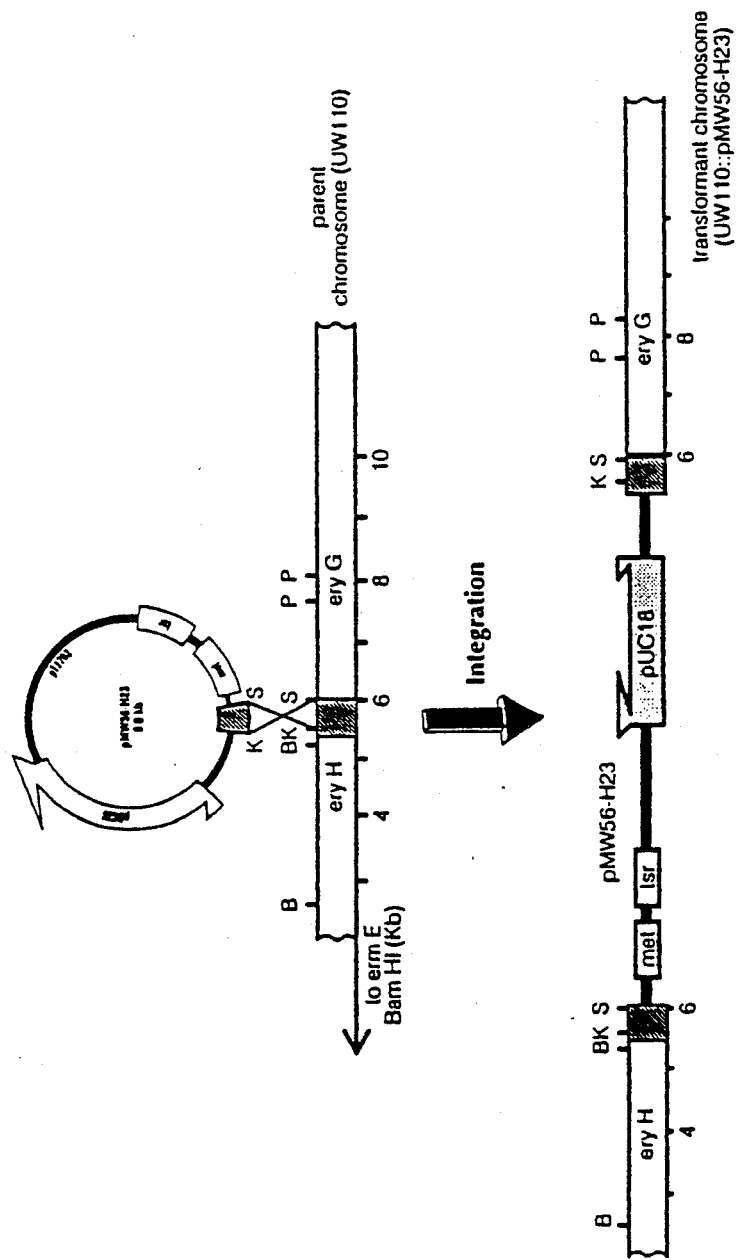
FIG. 6 is a schematic representation of the transformation of S. erythraea UW110 by the integration of plasmid pMW56-H23 containing an homologous DNA sequence.

Integration of a representative plasmid of the present invention into an erythromycin-producing host microorganism is schematically illustrated in FIG. 6. A recognition sequence (shaded) is homologous with a subset of the host gene for the C-6 hydroxylase enzyme. Recombination via crossing-over between the homologous sequences results in the stable integration of the plasmid, and is accompanied by the loss of 6-hydroxylation during erythromycin biosynthesis.

The present invention is versatile enough that any nucleotide sequence which is capable of being integrated into the *S. erythraea* genome via homologous recombination, so as to produce a transformant which is deficient in the cytochrome P450 monooxygenase system, can be substituted for the nucleotide sequence exemplified above. It should be understood that the DNA sequence inserted as a recognition sequence in the selected restriction site of the integrative plasmid may include nucleotides which are not part of the actual structural genesfor the cytochrome P450 monooxygenase system or may only include a fragment of those structural genes. Any regulatory genes found to control erythromycin biosynthesis may likewise be disrupted through the use of an integrative plasmid or other mutagenic technique, without departing from the scope of the invention.

The present invention further provides pharmaceutical compositions comprising a therapeutically effective amount of a compound of the invention in combination with a pharmaceutical carrier. By administering a therapeutically effective amount of the compositions of the invention, they may be used for the treatment and prevention of bacterial and other infections in human and other mammalian patients.

The compounds of the present invention include pharmaceutically acceptable salts and esters of the compounds of Formula I which can be made using conventional preparative techniques. The salts of the invention include those formed in reaction with organic acids such as an organic carboxylic acid (such as tartaric, citric, stearic or succinic acid), methanesulfonic acid, aminoethanesulfonic acid, an amino acid (such as aspartic or glutamic acid) or the like. These salts may be obtained by treating a compound of formula I with the corresponding acid. The above compounds are useful for the treatment and prevention of pathogenic infection in human and animal patients, in the manner in which erythromycins have been previously employed.

The compounds of the invention also include the biosynthetic intermediate 3-α-mycarosyl-6-deoxyerythronolide B which, like those disclosed above, may serve as a reactant in the synthesis of further macrolides of interest.

The compositions of the present invention are made by formulating a therapeutically effective amount of a compound of the invention together with a pharmaceutically acceptable carrier for parenteral injection, oral administration in solid or liquid form, rectal administration, and the like. By "therapeutically effective amount" is meant a sufficient amount of the compound to treat or prevent a susceptible bacterial or other microorganismal infection at a reasonable risk-to-benefit ratio. Total daily doses administered to a patient in single or divided doses can be in amounts, for example, of 1 to 100 mg/kg and more usually 5 to 50 mg/kg. Unit dosage composition may contain submultiples thereof to make up the desired daily dose.

The amount of active ingredient that can be combined with carrier materials to produce a single dosage form will vary depending upon the patient treated and the particular mode of administration. It is to be understood, moreover, that the effective amount of a compound of this invention will vary with the particular organism being treated or prevented; the severity of the infection; the duration of treatment; the specific compound, ester or salt being employed; the age and weight of the patient; and like factors well known in the medical art.

Compositions for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders, and granules. In such solid dosage forms, the active compound may be admixed with at least one inert diluent such as sucrose, lactose, or starch. Such dosage forms may also comprise, as is normal practice, pharmaceutical adjuvant substances such as stearate lubricating agents. In the case of capsules, tablet, and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants such as wetting, emulsifying, suspending, sweetening, flavoring, and perfuming agents.

The term "cytochrome P450 monooxygenase system" as used herein refers to a group of proteins (two flavoproteins, an iron-sulfur protein (erythrodoxin) and the C-6 hydroxylase enzyme) which function together to cause hydroxylation of 6-deoxyerythronolide B in *S. erythraea*.

The term "plasmid" as used herein refers to a small circular form of DNA that carries certain genes or portions of genes and is capable of replicating independently in a host microorganism.

The term "erythromycin biosynthetic gene cluster" as used herein refers to genes involved in erythromycin A biosynthesis located in the vicinity of the gene conferring erythromycin resistance.

The term "crossing-over" as used herein refers to a mechanism for exchanging genes between a microorganismal chromosome and homologous DNA contained in a plasmid through a process involving breakage and rejoining of DNA segments.

The term "homologous recombination" as used herein refers to complementary base-pairing and crossing-over between DNA strands containing identical or nearly identical sequences.

The term "*E. coli* origin of replication" as used herein refers to a DNA sequence that controls and allows for replication and maintenance of a plasmid or other vector in *E coli*.

The term "Streptomyces origin of replication" as used herein refers to a DNA sequence that controls and allows for replication and maintenance of a plasmid or other vector in Streptomyces.

The term "restriction fragment" as used herein refers to any linear DNA generated by the action of one or more restriction enzymes.

The term "transformation" as used herein refers to the introduction of DNA into a recipient microorganism that changes the genotype and consequently results in a change in the microorganism.

BACTERIAL STRAINS, PLASMID VECTORS, AND GROWTH MEDIA

The erythromycin-producing microorganism used to practice the following examples of the invention were wild-type derivatives of S. erythraea, formerly Streptcmyces erythreus NRRL 2338 (UW22, Weber et al., *J. Bacteriol.* 164:425-433 (1985)). The host strain in which integrative transformation was carried out was *S. erythraea* UW110 (met-4 leu-18 rif-63;. The host strain in which pIJ702 derivatives were replicated was *Streptomyces lividans* TK21 which was obtained from the John Innes Institute, Norwich, UK. The host strain for growth of *Escherichia coli*-derived plasmids was *E. coli* DH5-α from Bethesda Research Laboratories (BRL), Gaithersburg, MD.

Plasmid pIJ702 (Katz et al., *J. Microbiol.* 129:2703-2714 (1983)) was obtained from the John Innes Institute. Plasmid pUC18 was obtained from BRL. Cosmid pJI, which includes *S. erythraea* wild-type DNA containing the ermE gene was provided by L. Katz, J. Tuan and M. Staver of Abbott Laboratories. Plasmid pMW27, a multifunctional parent vector for integrative transformation in *S. erythraea*, was constructed from pIJ702 and pUC18 joined at their unique KpnI sites in the orientation with the EcoRI site of pUC18 closer to the BglII site of pIJ702.

*S. erythraea* was grown in liquid culture in 50 mL Tryptic Soy Broth (TSB, Sigma, St. Louis, MO) supplemented with 2% glycine in 500 mL shake flasks at 32° C. R2T2 agar plates (Weber, et al, 1988) were used for regeneration of mycelia from protoplasts or as a general sporulation medium. *S. erythraea* transformants were selected for using thiostrepton at 5 ug/mL (liquid culture) or 10 ug/mL (solid culture).

REAGENTS AND GENERAL METHODS

Commercially available reagents were used to make the compounds, plasmids and genetic variants of the present invention, including ampicillin, restriction endonucleases, T4-DNA ligase and calf intestinal alkaline phosphatase. Restriction enzymes and T4 DNA ligase were used according to suppliers' instructions regarding reaction conditions. Thiostrepton was obtained from E.R. Squibb and Sons, Princeton, NJ.

During preparation of the integrative plasmid, standard procedures were used for the growth and transformation of the intermediate host *E. coli* (Maniatis, et al., "Molecular Cloning, A Laboratory Manual", Cold Spring Harbor, N.Y. (1982)). The final transformation of *S. erythraea* was performed by a variation of the method of Weber, et al., *Gene* 68:173-180 (1988)), as detailed below.

The foregoing can be better understood by reference to the following examples, which are provided as non-limiting illustrations of the practice of the invention.

EXAMPLE 1

Construction of plasmid pMW27

Figure 2:
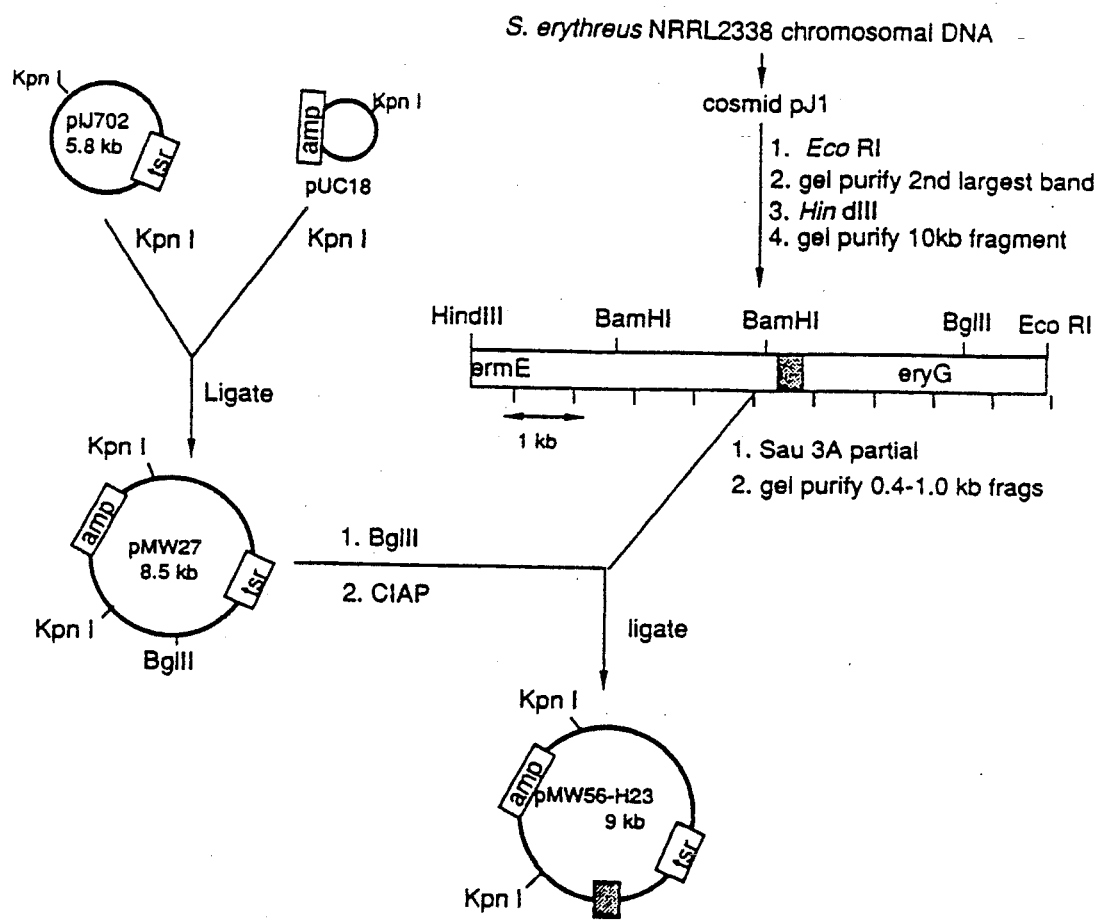
FIG. 2 is a flow diagram depicting the construction of plasmid pMW56-H23 from plasmid pMW27.

Plasmid pMW27 was constructed using standard methods of recombinant DNA technology according to the schematic outline shown in FIG. 2. Plasmid pUC18 from *E. coli* (Yanisch-Perron, et al., *Gene*, 33:103-119 (1985)) was completely digested with the restriction endonuclease KpnI. The resulting KpnI fragment was ligated to plasmid pIJ702 that had also been cleaved with KpnI (Katz et al., *J. Gen. Microbiol.* 129:2703-714 (1983)). The products of ligation were used to transform *E coli* DH5-α (Bethesda Research Labs., Gaithersberg, MD), which was the cultured in the presence of ampicillin to select for host cells carrying a recombinant plasmid. Plasmid DNA was isolated from individual transformants and characterized with respect to marker restriction sites, confirming the formation of the 8.5 kb recombinant plasmid pMW27.

EXAMPLE 2

Isolation of Fragments of the ermE region of *S. erythraea*

A portion of the *S. erythraea* genome responsible for the operation of the cytochrome P450 monooxygenase system was isolated using scanning gene disruption, which is modelled after mutational cloning described by Chater et al., *Gene* 26:67-78 (1983). This technique was utilized to probe the ermE-containing region of the *S. erythraea* chromosome.

As is the case for other antibiotic-producing organisms, the genes for the biosynthesis of erythromycin were thought to be clustered about the gene for resistance to erythromycin, ermE. To confirm this belief and to isolate the nucleotide sequences responsible for C-6 hydroxylation, cloned DNA fragments from the *S. erythraea* chromosome covering the region of interest were partially digested using the restriction endonucleases EcoR1 and HindIII. The resulting DNA fragments were separated by gel electrophoresis, purified from the agarose gel by Geneclean (Bio101, La Jolla, CA) and partially digested with the enzyme Sau3A. DNA fragments in the size range of approximately 0.2-1.0 kb were produced, and were again separated by gel electrophoresis, purified with Geneclean and ligated to pMW27 which had been digested with BglII. Ligation was facilitated by pre-treating the pMW27 digest with calf intestinal alkaline phosphatase.

The ligated recombinant plasmids were then used to transform *E. coli* DH5-α cells, which were then cultured on LB 0 agar supplemented with ampicillin (100 ug/ml) and X-gal (5'-bromo-4'-chloro-3'-indolyl-β-D-galactoside) to select for transformants carrying plasmids with inserts. These transformants were identified by colony blot hybridization (Maniatis, et al., 1982) using radiolabeled fragments of the original EcoRI-HindIII DNA sequence as probes. Plasmids with inserts were next integratively transformed into protoplasts of *S. erythraea* UW110. Primary transformants of *S. erythraea* were selected with 10 mg/mL of thiostrepton on R2T2 plates, and spores were harvested and combined in glycerol. Integrated transformants were isolated by either (a) plating a portion of the combined primary transformant spores onto R2T2, harvesting the lawn of spores and replating for single colonies on R2T2 plus thiostrepton, or (b) passing the combined spores of primary transformants through two to three single colony purifications on R2T2 plus thiostrepton.

To determine the location of the plasmid insertion, chromosomal DNA was prepared from the integratively transformed strains and the parent strain. The DNAs were compared by Southern analysis probing with the DNA fragment covering the region into which insertions were being made. Integration by homologous recombination was identified by the disappearance of a band in the parental DNA and the appearance of two new junction bands in the transformant DNA.

Figure 7:
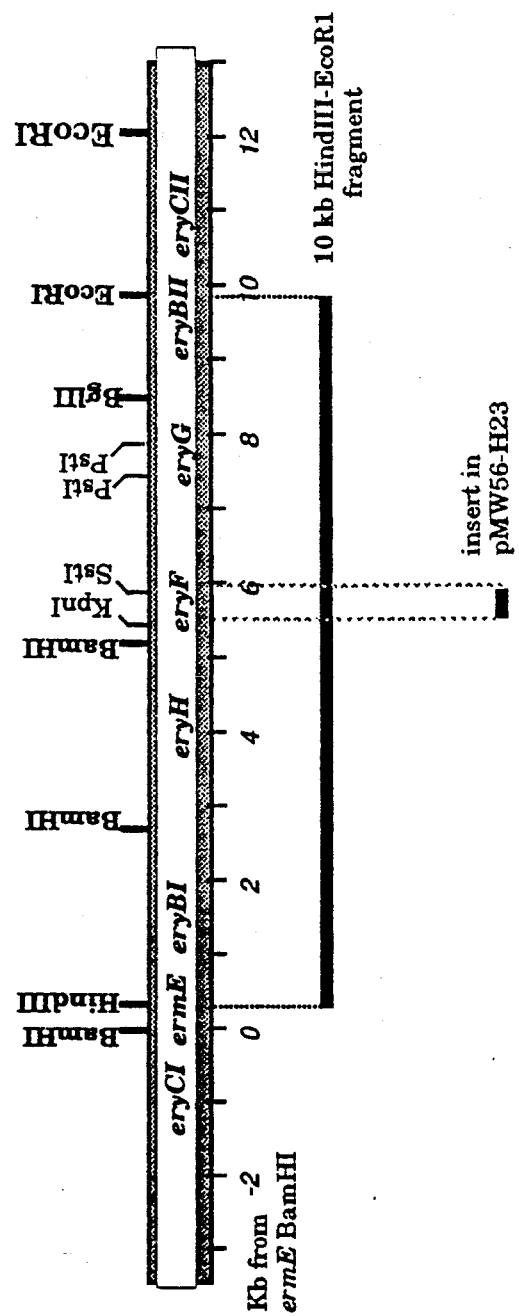
FIG. 7 is a chromosomal map of the S. erythraea genomic region containing the erythromycin biosynthetic gene cluster.

The resulting library consisted of approximately 350 clones which were shown through the above Southern blotting and restriction analysis to contain DNA fragments 0.4 to 1.0 kb in size. The fragments were found to be homologous to a 10 kb region of the *S. erythraea* chromosome, shown in the chromosome map of FIG. 7 to fall between the eryCI and eryCII genes. The gene responsible for C-6 hydroxylation, later designated eryF, was found to be positioned between the eryH and eryG genes.

EXAMPLE 3

Construction of Plasmid pMW56-H23

An integrative plasmid embodying the invention was prepared from plasmid pMW27 according to the schematic outline of FIG. 2. Cosmid pJI, which contained the ermE gene region of *S. erythraea* and approximately 30 kb of flanking DNA, was digested to completion with the restriction enzymes HindIII and EcoRI. From the products of digestion, a 10 kb DNA fragment was isolated which was identified as comprising the region from the HindIII site of ermE and sequences downstream of ermE up to the first EcoRI site beyond the eryG gene (Weber et al., 1989) (see FIG. 5). Using standard conditions (Maniatis et al., 1982), the 10 kb DNA fragment was subjected to partial digestion with Sau3A. DNA fragments of between 0.4 and 1.0 kb were separated using a preparative agarose gel and isolated with GeneClean (Bio101, LaJolla, CA). The DNA fragments were ligated to pMW27 which had been cleaved with the restriction enzyme BglII and treated with alkaline phosphatase (calf intestinal).

One plasmid, designated pMW56-H23, was selected for further examination based on its ability to generate transformants producing a compound of interest as identified by thin layer chromotography (TLC). Plasmid pMW56-H23 was found to contain a 503 bp DNA fragment originating from the eryF region of the *S. erythraea* chromosome and shown in FIG. 4 of the accompanying drawings. Further analysis of plasmid pMW56-H23 allowed the construction of the restriction site and functional map of plasmid pMW56-H23 which is shown in FIG. 5.

EXAMPLE 4

An example of the 6-deoxyerythromycin-producing microorganism of the resent invention was prepared by transforming *S. erythraea* cells with the recombinant plasmid of the previous Example. Transformation was carried out using *S. erythraea* protoplasts according to the following method. Under sterile conditions and a culture volume of 50 ml, three cultures of Saccharopolyspora erythraea UW110 (Weber et al., *J. Bacteriol.* 164:425-433 (1985)) were grown with shaking in Tryptic Soy Broth (TSB; Sigma, St. Louis, MO) plus 2% glycine at 32° C. for 3, 4 and 5 days, respectively, and then washed separately in 25 ml of 10.3% sucrose. The washed cells were then suspended in 25 ml PT buffer containing 2-5 mg/ml lysozyme, after which the suspensions were combined and incubated at 30° C. for 30-60 minutes until most mycelial fragments had been converted to spherical protoplasts. (PT buffer per 1 liter aqueous solution: 100 g sucrose, 5.08 g $MgCl_2 \cdot 6H_2O$, 0.25 g $K_2SO_4$, 2 ml trace elements (Hopwood et al., Methods Manual, 1985), and distilled water to 875 ml, with the addition, after sterilization and at time of use, of 25 ml 1M $CaCl_2 \cdot 2H_2O$ and 100 ml 0.25M TES (pH 7.2).)

The protoplasts were washed once and suspended in 10 ml of PT buffer. The protoplasts from 1 ml of the suspension were collected under light centrifugation ($1000 \times g$ for 15 minutes) and resuspended gently in the liquid remaining after decanting of the PT supernatant. Transformation was carried out by adding about 5 ul (5 ug) of plasmid pMW56-H23 and 0.5 ml of 25% PEG (polyethylene glycol, MW 3350, Sigma, St. Louis, MO) to the protoplast suspension. The protoplasts were washed and resuspended in 0.5-1.0 ml of PT buffer. 200 ul volumes of the transformed protoplasts were plated on 25 ml of R2T2 regeneration agar (Weber et al., 1989). The plates were incubated overnight at 32° C., then overlayed with 2.5 ml of soft nutrient agar (0.3% bacto-agar, 0.8% difco nutrient broth) containing 100 ug/ml thiostrepton and reincubated at 32° C. until transformants appeared and sporulated. In order to isolate a pure integratedtransformant strain, spores of the primary transformants were collected and streaked twice for single colonies on R2T2 agar containing 10 ug/ml thiostrepton. The resultant colonies were conventionally cultured and constituted the desired *S. erythraea* UW110::pMW56-H23 transformants.

EXAMPLE 5

Construction of Saccharopolyspora erythraea 41R

A preferred example of the 6-deoxyerythromycin-producing microorganism of the present invention was prepared by conducting a genetic cross between the above transformant *S. erythraea* UW110::pMW56-H23 and another strain known to produce high levels of erythromycin A. The cross was performed as follows: Spore suspensions of each of the two parent strains ($10^8$ spores/ml in 20% glycerol) were mixed in equal proportions and 0.1 ml portions of the mixture plated on E20A agar medium. (E20A medium per 1 liter aqueous solution: 5 g bacto-soytone, g soluble starch, 3 g $CaCO_3$, 2.1 g MOPS, and 20 g agar.) The plates were incubated at 32° C. until sporulation occured (5-7 days). The resulting spores were harvested, suspended in 20% glycerol at $10^8$ spores/ml, and plated for recombinants on AVMM medium containing 10 ug/ml thiostrepton. (AVMM medium per 1 liter aqueous solution: 1 g $K_2HPO_4$, 1 g $KH_2PO_4$, 0.1 g $MgSO_4$, 10 mg $FeSO_4$, and 5 g asparagine, to which are added, after sterilization, 20 ml 50% glucose, 0.5 mg each of thiamine, riboflavin, pantothenic acid, nicotinic acid and pyridoxine, and 0.05 mg each of folic acid, biotin and vitamin B-12.)

The progeny producing 6-deoxyerythromycins were selected by virtue of their ability to grow on AVMM medium in the presence of thiostrepton. A number of recombinants were isolated and screened, using TLC, for elevated levels of production of 6-deoxyerythromycins. One isolate, designated 41R, was found to produce the compounds of the invention at significantly higher levels than those obtained from the parent transformant.

EXAMPLE 6

Fermentation of *Saccharoposyspora erythraea* 41R

The recombinant *S. erythraea* 41R, produced in the previous Example, was cultivated to larger quantities using the following fermentation procedure. Spores of *S. erythraea* 41R were taken from E20A agar medium slants of the organism and added to 50 ml of E29F medium in a 500 ml Erlenmeyer shake flask. (E29F medium per 1 liter aqueous solution: 22 g soy flour, 15 g corn starch, 3 g $CaCO_3$, 0.5g $MgSO_4 \cdot 7H_2O$, 15 mg $FeSO_4 \cdot 7H_2O$, and 50 ml soybean oil.) The first stage culture was then incubated while shaking for 48 hours at 32° C. Following incubation, 1 ml portions of the first stage culture were used to inoculate 50 second stage fermentation flasks also containing E29F medium. These cultures were then grown with shaking for 5 days at 32° C.

On the fifth day the cultures were combined and the cells separated from the culture broth by centrifugation. The culture broth was adjusted to pH 10 with a solution of 4N NaOH and treated with an equal volume of ethyl acetate to extract the compounds of the present invention.

EXAMPLE 7

Isolation of Compounds

Several of the compounds of the present invention were isolated using the following procedure. The ethyl acetate extract from 1150 ml of whole fermentation broth, prepared as described in the previous Example, was adjusted to pH 9 and concentrated to an oil. The concentrate was partitioned between 150 ml each of heptane and methanol and the lower methanol layer was concentrated to 1.74 gm of residue. The residue was chromatographed on a Sephadex LH-20 column (3.2 cm×75 cm) which waspre-swollen with a mixture of chloroform, heptane, ethanol (10:10:1, v/v/v) and loaded and eluted with the same solvent. Ten mL fractions were collected and analyzed by TLC on silica gel plates (Merck Kieselgel $60F_{254}$) developed with a solvent system of isopropyl ether, methanol, and concentrated ammonium hydroxide (150:70:4, v/v/v). Spots were visualized on the dried plates by heating the plate after spraying with anisaldehyde 5% in ethanol:sulfuric acid (19:1, v/v)). Fraction numbers 30-32 showed a magenta spot having an Rf similar to that of erythromycin A, the Rf of which varies from approximately 0.25 to approximately 0.6. These fractions were combined and concentrated to a residue hereinafter designated residue A (38 mg). Subsequent fraction numbers 33-38 were concentrated to a residue hereinafter designated as residue B (77.5 mg).

Residue A was chromatographed in two portions on an Ito Coil Planet Centrifuge in a solvent system consisting of carbon tetrachloride, methanol, and 0.01 M aqueous potassium phosphate buffer pH 7.0 (1:1:1), under the following conditions: upper phase mobile; tail as inlet; approximately 3 mL/min flow rate at 800 rpm; and approximately 60% stationary phase retention. 10 ml fractions were collected. Mobile phase breakthrough occurred at fraction 12. The fractions were assayed for bioactivity with an agar disk diffusion assay on pH 8 plates seeded with Staphylococcus aureus 6538P and by TLC as above. Like fractions were combined, concentrated, and partitioned between methylene chloride and dilute ammonium hydroxide (pH 9). The methylene chloride layers were concentrated to solid residues. Fraction numbers 32 to 42 yielded a total of 9 mg of a white solid later identified as 6-deoxyerythromycin C. Fractions 100 to 135 yielded a total of 13.4 mg of a white solid later identified as 6-deoxyerythromycin A.

Residue B was chromatographed under identical conditions on an Ito Coil Planet Centrifuge. Fraction numbers 10-15 yielded 1.8 mg of 6-deoxy-15-norerythromycin C (having the PMR spectrum shown in FIG. 12), while fractions 32-40 yielded 4.2 mg of 6-deoxyerythromycin C and fractions 125-135 yielded 10.1 mg of 6-deoxyerythromycin A.

EXAMPLE 8

Isolation of Additional Compounds

New cultures of S. erythraea 41R were grown according to the techniques of Example 6 except that a 1.25-fold more concentrated form of E29F medium was employed using 40 ml instead of 50 ml per flask. After growth, the cultures were combined and extracted with ethyl acetate. The ethyl acetate fraction was concentrated to a residue (3.71 g), and the residue chromatographed on a column of Sephadex LH-20 (65×5 cm) packed and eluted with n-heptane, chloroform, and ethanol (10:10:1, v/v/v). Fractions were analyzed as described in Example 7. Early fractions were combined to give 220 mg of a white, glassy residue hereinafter referred to as residue C. Later fractions were combined to give a second white, glassy residue, hereinafter referred to as residue D.

Residue C was chromatographed on an Ito Coil Planet Centrifuge in a solvent system of carbon tetrachloride, methanol, and 0.01 M aqueous potassium phosphate buffer, pH 7.0 (1:1:1, v/v/v) employing the following conditions: lower phase mobile; tail as inlet; approximately 5 mL/min flow rate at 800 rpm; 10mL fractions were collected. The upper phase displacement from an approximately 325 mL column was about 50 mL. Fractions of approximately 10 mL each were analyzed by TLC and combined accordingly. Fraction No. 6 was concentrated and yielded 6-deoxyerythromycin B (20.4 mg). Fraction numbers 8 and 9 were combined and concentrated to yield 6-deoxy-15-norerythromycin B (21.4 mg).

Residue D was chromatographed on a Sephadex LH-20 column in methanol. Fractions were collected and analyzed by TLC. Initial fractions were combined to yield a glassy residue which was chromatographed on an Ito Coil Planet Centrifuge in a solvent system of carbon tetrachloride, methanol, and 0.05 M aqueous potassium phosphate buffer, pH 6.0 (1:1:1, v/v/v) with the lower phase mobile in the tail to head mode. Approximately 10mL fractions were collected. Fractions were analyzed by TLC and combined accordingly. Fractions 46-58 were combined and concentrated to yield 6-deoxyerythromycin D (26.2 mg).

EXAMPLE 9

Isolation of Additional Compounds

Using the techniques of the previous Examples, ethyl acetate was used to extract approximately 1200 mL of whole fermentation broth from a culture of a high-producing recombinant cross of the invention. The ethyl acetate fraction was concentrated to an oily residue which was partitioned between 200 mL of n-heptane and 200 mL methanol. The methanolic layer was concentrated to an oily residue (3.98 g). A 2.0 g portion of this residue was chromatographed on a Sephadex LH-20 column which was preswollen with a mixture of chloroform, heptane, and ethanol (10:10:1, v/v/v) and loaded and eluted with the same solvent. Fractions (approximately 10 mL each) were collected and analyzed as in Example 7. Fractions 70-160 yielded 350 mg of a white glassy solid hereinafter referred to as residue E.

Residue E was chromatographed on an Ito Coil Planet Centrifuge in a solvent system consisting of carbon tetrachloride, methanol, and 0.01 M aqueous potassium phosphate buffer, pH 7.0 (1:1:1, v/v/v) under the following conditions: upper phase mobile; tail as inlet; 800 rpm; approximately 3 mL/min flow rate; approximately 80% stationary retention. 10 mL fractions were collected. Fractions were analyzed by TLC as described in Example 7 and combined accordingly. Combined fractions were adjusted to pH9 with concentrated aqueous ammonium hydroxide and extracted twice with equal volumes of methylene chloride. The methylene chloride extracts were washed once with water and then concentrated to yield the following products as clear glassy solids: fractions 38-40 yielded 3.2 mg of 6-deoxyerythromycin C; fractions 48-50 yielded 1.9 mg of 6-deoxy-15-norerythromycin A; fractions 75-80 yielded 0.9 mg of 6-deoxy-I5-norerythromycin D; and fractions 95-121yielded 3.8 mg of 6-deoxyerythromycin A.

EXAMPLE 10

Figure 8:
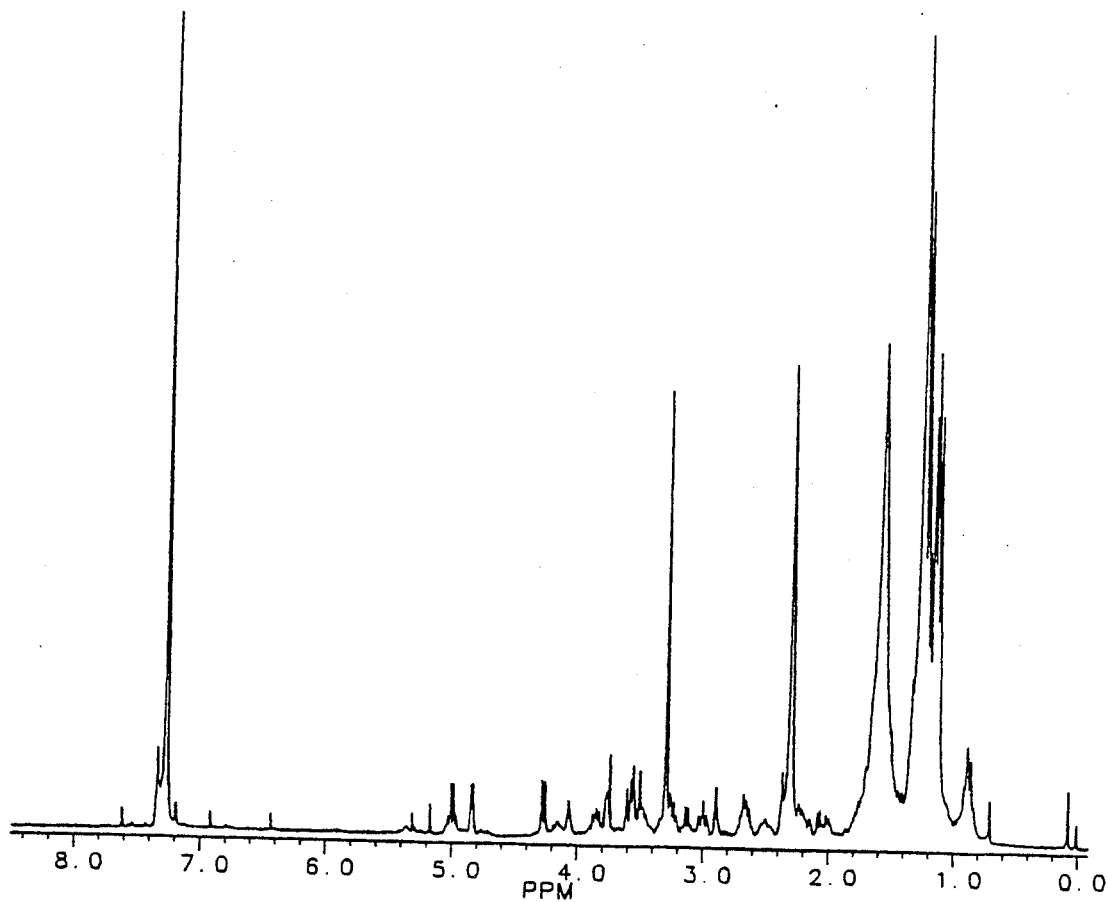
FIGS. 8 and 9 are 500 MHz $^1$H NMR spectra of 6-deoxy15-norerythromycins A and C, respectively.
Figure 9:
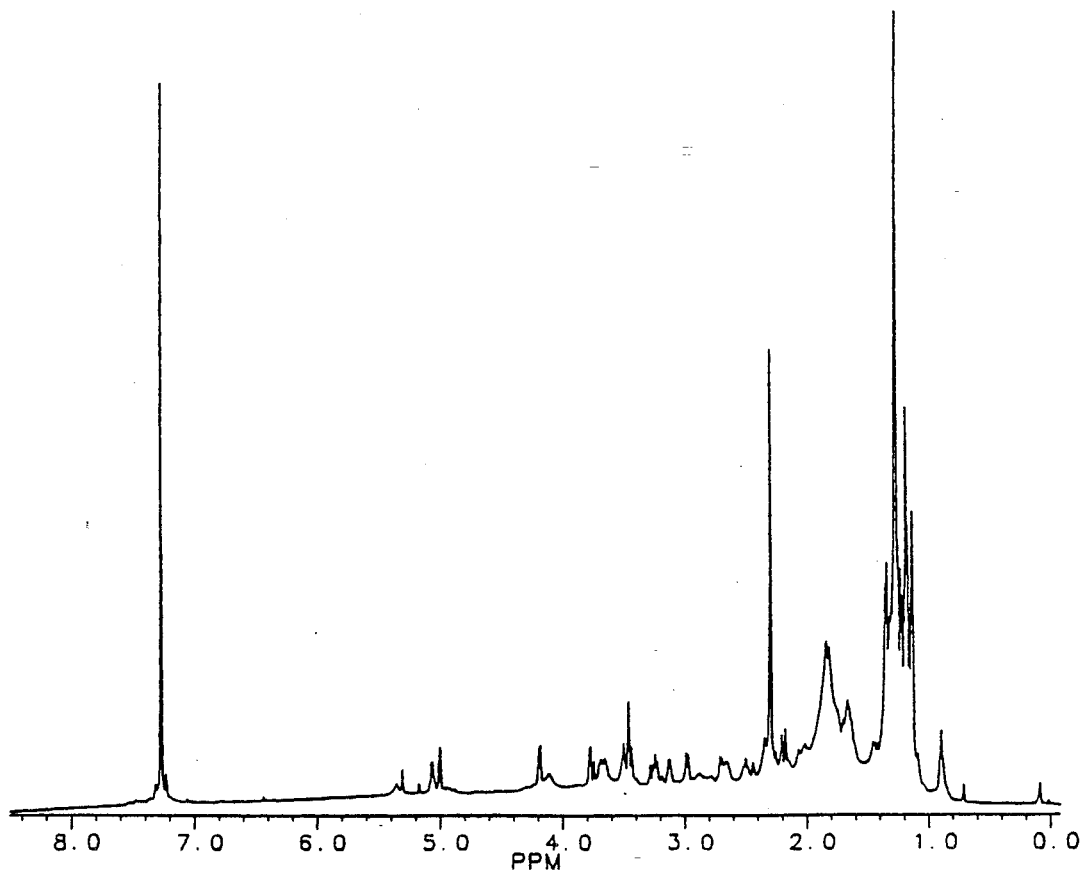

Characterization of 6-Deoxverythromycins A, B, C and D, and 6-Deoxy-15-norerythromycins B, and D The compounds isolated in the previous examples were identified using high resolution Fast Atom Bombardment (FAB) mass spectrometry, proton NMR and $^{13}$C-NMR. The results of those studies, including $^{13}$C and proton magnetic resonance chemical shift data, were tabulated for 6-deoxyerythromycins A, B, C and D and 6-deoxy-15-norerythromycins B and D, and are listed in Tables 2 and 3, respectively. Assignments for the carbon and proton magnetic resonances were made with the aid of 2D NMR experiments. Proton NMR spectra for 6-deoxy-15-norerythromycins A and C were not tabulated but are shown in FIGS. 8 and 9, respectively.

Infrared absorption spectra and optical rotations were also obtained for these compounds and are summarized as follows:

The optical rotations for 6-deoxyerythromycins A, B, C and D are $[\alpha]^{23}_D$ −54.8 (c 0.5, CHCl$_3$), −74.3 (c 1.2, CHCl$_3$), −41.0 (c 1.0, CHCl$_3$), and −77.9 (c 1.3, CHCl$_3$), respectively. Optical rotations for 6-deoxy-15-norerythromycins B and D are $[\alpha]^{23}_D$−84.1 (c 1.1, CHCl$_3$) and −83.3 (c 0.4, CHCl$_3$), respectively.

Infrared spectroscopic (IR) data for 6-deoxyerythromycin A indicate the following values (cm−1) in CDCl$_3$ solution: 3700, 3550, 3450 broad shoulder, 1728 strong, 1705, 1685 shoulder, 1600 weak; 6-deoxyerythromycins B and D in CDCl$_3$: 3680 weak, 3540 broad, 1722, 1702 strong; 6-deoxyerythromycin C in CDCl$_3$: 3700, 3520 strong, broad, 1728 strong, 1705, 1685 shoulder, 1600 weak; 6-deoxyerythromycin D in CDCl3: solution 3680, 3570 strong broad, 1722, 1700 strong; and 6-deoxy-15-norerythromycin D in CDCl3: 3630, 3510 strong broad, 1725, 1702 strong broad.

TABLE 1

| Compound | m/z | Calculated Formula | Calculated Molecular Weight |
|---|---|---|---|
| No. 1 | 718.75* | C$_{37}$H$_{68}$NO$_{12}$ | 718.4741 |
| No. 2 | 702.4785 | C$_{37}$H$_{68}$NO$_{11}$ | 702.4792 |
| No. 3 | 704.75* | C$_{36}$H$_{66}$NO$_{12}$ | 704.4585 |
| No. 4 | 688.4650 | C$_{36}$H$_{66}$NO$_{11}$ | 688.4636 |
| No. 5 | 688.4628 | C$_{36}$H$_{66}$NO$_{11}$ | 688.4636 |

TABLE 1-continued

| Compound | m/z | Calculated Formula | Calculated Molecular Weight |
|---|---|---|---|
| No. 6 | 674.4439 | C$_{35}$H$_{64}$NO$_{11}$ | 674.4479 |

No. 1 = 6-deoxyerythromycin A
No. 2 = 6-deoxyerythromycin B
No. 3 = 6-deoxyerythromycin C
No. 4 = 6-deoxyerythromycin D
No. 5 = 6-deoxy-15-norerythromycin B
No. 6 = 6-deoxy-15-norerythromycin D.
*Low resolution measurement

TABLE 2

Tabulation of $^{13}$C Chemical Shifts for 6-Deoxyerythromycins A-D and 6-Deoxy-15-norerythromycins B and D

| | A | B | C | D | E | F |
|---|---|---|---|---|---|---|
| 1 | 176.8 | 177.4 | 176.5 | 177.1 | 177.0 | 176.7 |
| 2 | 45.0 | 45.0 | 45.2 | 45.0 | 44.7 | 44.9 |
| 3 | 78.4 | 80.2 | 81.2 | 82.8 | 79.2 | 82.1 |
| 4 | 44.2 | 43.3 | 44.0 | 44.0 | 43.4 | 43.2 |
| 5 | 83.4 | 84.2 | 84.2 | 84.9 | 84.0 | 84.8 |
| 6 | 35.1 | 36.7 | 35.2 | 36.7 | 35.7 | 36.1 |
| 7 | 34.4 | 34.3 | 34.2 | 34.2 | 34.3 | 34.2 |
| 8 | 45.7 | 45.1 | 45.8 | 45.1 | 45.2 | 45.3 |
| 9 | 220.1 | 216.8 | 220.0 | 216.7 | 217.4 | 217.2 |
| 10 | 38.9 | 41.6 | 38.7 | 41.5 | 41.1 | 41.2 |
| 11 | 69.6 | 70.1 | 69.5 | 70.1 | 70.3 | 70.5 |
| 12 | 75.0 | 40.5 | 74.9 | 40.6 | 41.9 | 42.0 |
| 13 | 77.6 | 76.0 | 76.4 | 76.4 | 70.4 | 70.6 |
| 14 | 21.1 | 25.4 | 20.9 | 25.4 | 18.1 | 18.3 |
| 15 | 11.0 | 10.5 | 10.9 | 10.5 | — | — |
| 2CH$_3$ | 15.0 | 15.1 | 15.4 | 15.3 | 14.2 | 14.6 |
| 4CH$_3$ | 9.5 | 9.4 | 9.7 | 9.7 | 9.5 | 9.7 |
| 6CH$_3$ | 18.7 | 19.9 | 18.7 | 20.0 | 19.5 | 19.8 |
| 8CH$_3$ | 17.4 | 16.7 | 17.4 | 16.7 | 16.7 | 16.8 |
| 10CH$_3$ | 11.0 | 7.8 | 10.9 | 7.7 | 7.9 | 7.8 |
| 12CH$_3$ | 16.1 | 9.0 | 16.1 | 9.1 | 8.6 | 8.7 |
| 1' | 104.1 | 104.2 | 104.9 | 105.0 | 104.2 | 105.0 |
| 2' | 70.7 | 70.6 | 70.5 | 70.5 | 70.6 | 70.4 |
| 3' | 65.6 | 65.6 | 65.7 | 65.8 | 65.7 | 65.7 |
| 4' | 28.6 | 29.1 | 28.4 | 28.5 | 28.8 | 28.5 |
| 5' | 69.2 | 69.0 | 69.5 | 69.4 | 69.1 | 69.4 |
| 6' | 21.3 | 21.1 | 21.3 | 21.2 | 21.4 | 21.2 |
| N(CH$_3$)2 | 40.3 | 40.3 | 40.3 | 40.3 | 40.3 | 40.2 |
| 1" | 96.7 | 97.6 | 99.2 | 99.8 | 97.0 | 99.5 |
| 2" | 35.0 | 35.2 | 40.5 | 40.6 | 35.1 | 40.6 |
| 3" | 72.6 | 72.5 | 69.5 | 69.5 | 72.5 | 69.6 |
| 4" | 78.0 | 78.0 | 76.4 | 76.4 | 78.0 | 76.4 |
| 5" | 65.7 | 65.7 | 66.5 | 66.6 | 65.6 | 66.6 |
| 6" | 18.2 | 18.1 | 18.0 | 18.0 | 18.2 | 18.0 |
| 3"CH$_3$ | 21.5 | 21.4 | 25.5 | 25.5 | 21.2 | 25.6 |
| OCH$_3$ | 49.4 | 49.3 | — | — | 49.3 | — |

A = 6-Deoxyerythromycin A
B = 6-Deoxyerythromycin B
C = 6-Deoxyerythromycin C
D = 6-Deoxyerythromycin D
E = 6-Deoxy-15-norerythromycin B
F = 6-Deoxy-15-norerythromycin D

TABLE 3

| PROTON | PMR Assignments | | | | | |
|---|---|---|---|---|---|---|
| | A | B | C | D | E | F |
| 2 | 2.80 | 2.86 | 2.83 | 2.90 | 2.78 | 2.82 |
| 3 | 3.65 | 3.64 | 3.70 | 3.71 | 3.68 | 3.74 |
| 4 | 1.60 | 1.72 | 1.60 | 1.74 | 1.76 | 1.76 |
| 5 | 3.48 | 3.44 | 3.42 | 3.40 | 3.48 | 3.42 |
| 6 | 1.36 | 1.54 | 1.33 | 1.53 | 1.55 | 1.53 |
| 7a | 1.69 | 1.81 | 1.68 | 1.81 | 1.80 | 1.80 |
| 7b | 1.53 | 1.26 | 1.57 | 1.30 | 1.32 | 1.35 |
| 8 | 2.63 | 2.60 | 2.62 | 2.61 | 2.61 | 2.62 |
| 10 | 3.07 | 2.84 | 3.06 | 2.85 | 2.90 | 2.90 |
| 11 | 3.40 | 3.54 | 3.34 | 3.52 | 3.55 | 3.51 |
| 12 | — | 1.69 | — | 1.71 | 1.60 | 1.63 |
| 13 | 4.93 | 5.15 | 4.94 | 5.17 | 5.40 | 5.44 |
| 14a | 1.93 | 1.76 | 1.93 | 1.78 | 1.27 | 1.29 |
| 14b | 1.50 | 1.48 | 1.50 | 1.49 | — | — |
| 15 | 0.89 | 0.90 | 0.88 | 0.91 | — | — |
| 2CH$_3$ | 1.19 | 1.19 | 1.22 | 1.22 | 1.18 | 1.21 |

TABLE 3-continued

| | PMR Assignments | | | | | |
|---|---|---|---|---|---|---|
| PROTON | A | B | C | D | E | F |
| 4CH$_3$ | 1.17 | 1.17 | 1.13 | 1.14 | 1.17 | 1.15 |
| 6CH$_3$ | 1.17 | 1.21 | 1.18 | 1.24 | 1.21 | 1.23 |
| 8CH$_3$ | 1.18 | 1.13 | 1.19 | 1.17 | 1.15 | 1.16 |
| 10CH$_3$ | 1.15 | 1.01 | 1.16 | 1.02 | 1.00 | 1.02 |
| 12CH$_3$ | 1.10 | 0.83 | 1.10 | 0.84 | 0.86 | 0.87 |
| 1' | 4.23 | 4.20 | 4.17 | 4.17 | 4.21 | 4.18 |
| 2' | 3.25 | 3.24 | 3.22 | 3.21 | 3.23 | 3.20 |
| 3' | 2.48 | 2.56 | 2.46 | 2.48 | 2.52 | 2.50 |
| 4'a | 1.25 | 1.28 | 1.25 | 1.25 | 1.26 | 1.26 |
| 4'e | 1.67 | 1.72 | 1.68 | 1.67 | 1.69 | 1.68 |
| 5' | 3.46 | 3.46 | 3.49 | 3.48 | 3.46 | 3.48 |
| 6' | 1.24 | 1.23 | 1.24 | 1.23 | 1.23 | 1.23 |
| N(CH$_3$)2 | 2.29 | 2.34 | 2.28 | 2.28 | 2.30 | 2.29 |
| 1" | 4.88 | 4.83 | 5.03 | 4.99 | 4.81 | 4.98 |
| 2"a | 1.55 | 1.55 | 1.83 | 1.86 | 1.54 | 1.84 |
| 2"e | 2.36 | 2.36 | 2.20 | 2.20 | 2.33 | 2.19 |
| 4" | 3.00 | 2.99 | 2.98 | 2.98 | 2.97 | 2.98 |
| 5" | 3.92 | 3.93 | 3.76 | 3.78 | 3.89 | 3.77 |
| 6" | 1.28 | 1.27 | 1.34 | 1.34 | 1.26 | 1.34 |
| OCH$_3$ | 3.28 | 3.26 | — | — | 3.26 | — |
| 3"CH$_3$ | 1.12 | 1.22 | 1.26 | 1.25 | 1.22 | 1.26 |

A = 6-Deoxyerythromycin A
B = 6-Deoxyerythromycin B
C = 6-Deoxyerythromycin C
D = 6-Deoxyerythromycin D
E = 6-Deoxy-15-norerythromycin B
F = 6-Deoxy-15-norerythromycin D

EXAMPLE 11

Acid stability of 6-Deoxyerythromycin A

The relative acid stability of one of the compounds of the present invention was compared to that of erythromycin A. 11.8 mg of 6-deoxyerythromycin A was suspended in citric acid solution (pH 2.2) and allowed to remain at 37° C. for 8 hours. Aliquots were removed at 2, 5, 10, and 20 minutes and at 1, 2, 3, 4, 5, 6 and 8 hours. Degradation was quenced by adjusting each aliquot to pH 9.6 with 7.5 N NH$_4$OH, followed by extraction with methylene chloride.

10.5 mg of erythromycin A was identically suspended in critic acid solution (pH 2.0) and allowed to remain at 37° C. for 10 minutes. Aliquots were removed at 2, 5 and 10 minutes. Degradation was quenched by adjusting each aliquot to pH 9.6 with 7.5 N NH$_4$OH, followed by extraction with methylene chloride.

The methylene chloride extracts from 6-deoxyerythromycin A and erythromycin A were analyzed by TLC as described in Example 7. TLC results indicated that less than 10% of the erythromycin A remained after 2 minutes at pH 2.2, while more than 50% of 6-deoxyerythromycin A persisted after 4 hours of exposure to pH 2.2. Even after 8 hours, approximately 40% of 6-deoxyerythromycin A was found to remain intact, demonstrating the substantial acid stability improvement of the compounds of the present invention over erythromycin A itself.

EXAMPLE 12

Antibacterial Activity

6-Deoxyerythromycins A, B and C and 6-deoxy-15-norerythromycin B were tested for antibacterial activity using a standard agar plate dilution method in brain heart infusion broth. Erythromycin A was utilized as a control. The results, indicated as the minimum inhibitory concentrations (MICs) are shown in Tables 4 and 5, below.

TABLE 4

| | Antibacterial Spectrum MIC value (mcg/ml) | | |
|---|---|---|---|
| Microorganism | A | dA | dC |
| Staphylococcus aureus ATCC 6538P | 0.25 | 1 | 2 |
| Staphylococcus aureus NCTC 10649 | 0.25 | 1 | 2 |
| Staphylococcus aureus CMX 553 | 0.25 | .5 | 4 |
| Staphylococcus epidermis 3519 | 0.5 | 1 | 4 |
| Micrococcus luteus ATCC 9341 | 0.03 | 0.06 | 0.25 |
| Streptococcus agalactiae CMX 508 | 0.06 | 0.12 | 0.25 |
| Streptococcus pyogenes EES61 | 0.03 | 0.25 | 0.5 |
| Escherichia coli JUHL | 64 | >128 | >128 |
| Eschericha coli SS | 1 | 2 | 16 |
| Enterococcus faecium ATCC 8043 | 0.12 | 0.25 | 0.25 |

A = Erythromycin A
dA = 6-Deoxyerythromycin A
dC = 6-Deoxyerythromycin C

TABLE 5

| | Antibacterial spectrum MIC value (mcg/ml) | | | |
|---|---|---|---|---|
| Microorganism | A | B | dB | dnB |
| Staphylococcus aureus ATCC 6538P | 0.12 | 0.25 | 1 | 2 |
| Staphylococcus aureus NCTC 10649 | 0.12 | 0.25 | 1 | 2 |
| Staphylococcus aureus CMX 553 | 0.12 | 0.25 | 1 | 2 |
| Staphylococcus epidermis 3519 | 0.12 | 0.25 | 1 | 2 |
| Micrococcus luteus ATCC 9341 | 0.015 | 0.03 | 0.12 | 0.25 |
| Streptococcus agalactiae CMX 508 | 0.03 | 0.03 | 0.25 | 0.5 |
| Streptococcus pyogenes EES61 | 0.015 | 0.03 | 0.12 | 0.25 |
| Escherichia coli JUHL | 32 | 32 | >128 | >128 |
| Eschericha coli SS | 1 | 2 | 4 | 2 |
| Enterococcus faecium ATCC 8043 | 0.06 | 0.12 | 0.5 | 2 |

A = Erythromycin A
B = Erythromycin B
dB = 6-Deoxyerythromycin B
dnB = 6-Deoxy-15-norerythromycin B

EXAMPLE 13

In Vivo Antibacterial Activity

The in vivo activity of 6-deoxyerythromycin A was evaluated using the acute mouse protection test. Mouse mortality was used to calcualte an ED$_{50}$ value, i.e., the dose of drug required to protect 50% of the test animals against death due to inoculum challenge.

The acute mouse protection test was conducted as described by Fernandes, et al. (*Antimicrob. Agents Chemother.* 29:201–208(1986)) on female CF-1 mice weighing 20–25 grams. The mice were injected intraperitoneally with bacterial suspensions at a concentration 100 times that producing an LD$_{50}$ response. 6-Deoxyerythromycin A or erythromycin A were administered orally at 1 and 5 hours post-infection. The median effective doses for the cumulative mortalities on the sixth day after infection were calculated using a trimmed logit analysis (Hamilton, et. al., *Environ Sci. Technol.* 11:714–719 (1977)). The results of that analysis, shown in Table 6 below, indicate that 6-deoxyerythromycin A is as effective as erythromycin A when orally administered against murine infections of Staphylococci and Streptococci.

TABLE 6

| In-Vivo Activity of 6-Deoxyerythromycin A Following Oral Administration (Dose Providing 50% Survival, in mg/kg) | | |
|---|---|---|
| Bacterial Strain | dA | A |
| Staphylococcus aureus 10649 | 90.8 | 119.6 |
| Streptococcus pneumoniae 6303 | 24.9 | 24.8 |

TABLE 6-continued

In-Vivo Activity of 6-Deoxyerythromycin A Following
Oral Administration (Dose Providing 50% Survival, in mg/kg)

| Bacterial Strain | dA | A |
| --- | --- | --- |
| *Streptococcus pyogenes* C203 | 32.4 | 54.5 | dA = 6-deoxyerythromycin A
A = erythromycin A

What is claimed is:

1. A compound having the formula:

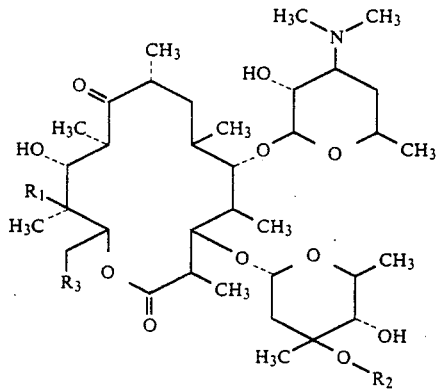

wherein $R_1$ is selected from the group consisting of OH and H, and $R_2$ and $R_3$ are independently selected from the group consisting of H and $CH_3$, or a pharmaceutically acceptable salt or ester thereof.

2. A compound selected from the group consisting of 6-deoxyerythromycins A, B, C and D, 6-deoxy-15-noreythromycins A, B, C and D, and the pharmaceutically acceptable salts and esters thereof.

3. A fermentation isolate obtained by culturing a microorganism, comprising a compound having the formula:

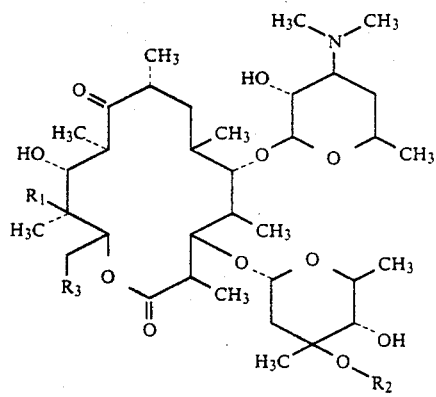

wherein $R_1$ is selected from the group consisting of OH and H, and $R_2$ and $R_3$ are independently selected from the group consisting of H and $CH_3$.

4. The fermentation isolate of claim 3 wherein the compound is selected from the group consisting of 6-deoxyerythromycins A, B, C and D and 6-deoxy-15-norerythromycins A, B, C and D.

5. A pharmaceutical composition comprising a thereapeutically effective amount of a compound according to claim 1 in combination with a pharmaceutical carrier.

6. A method of treating bacterial infections in a patient in need of such treatment, comprising administering to the patient a thereapeutically effective amount of a compound of claim 1.

* * * * *